US008316861B2

(12) United States Patent
Brewer et al.

(10) Patent No.: US 8,316,861 B2
(45) Date of Patent: Nov. 27, 2012

(54) SYSTEM AND METHOD FOR GUIDING A MEDICAL INSTRUMENT WITH MAGNETIC FORCE CONTROL

(75) Inventors: Reuben Brewer, Millbrae, CA (US); J. Kenneth Salisbury, Jr., Mountain View, CA (US); Kevin E. Loewke, Menlo Park, CA (US); David B Camarillo, Aptos, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 612 days.

(21) Appl. No.: 12/603,387

(22) Filed: Oct. 21, 2009

(65) Prior Publication Data
US 2010/0105984 A1 Apr. 29, 2010

Related U.S. Application Data

(60) Provisional application No. 61/107,264, filed on Oct. 21, 2008.

(51) Int. Cl.
*A61B 19/00* (2006.01)
*A61B 1/04* (2006.01)
*A61B 1/00* (2006.01)
*A61B 5/05* (2006.01)

(52) U.S. Cl. ........ 128/899; 600/117; 600/118; 600/114; 600/407; 600/424; 335/209

(58) Field of Classification Search .................. 600/117, 600/118, 114, 407, 424, 40; 128/899; 335/209
See application file for complete search history.

(56) References Cited

U.S. PATENT DOCUMENTS

| | | | | |
|---|---|---|---|---|
| 5,681,260 A * | 10/1997 | Ueda et al. | ..................... | 600/114 |
| 6,459,924 B1 * | 10/2002 | Creighton et al. | ............ | 600/427 |
| 2002/0188174 A1 * | 12/2002 | Aizawa et al. | ................ | 600/118 |
| 2004/0230271 A1 * | 11/2004 | Wang et al. | ................... | 607/116 |
| 2007/0244388 A1 * | 10/2007 | Sato et al. | ..................... | 600/424 |
| 2008/0091193 A1 * | 4/2008 | Kauphusman et al. | ......... | 606/41 |
| 2010/0036190 A1 * | 2/2010 | Murphy et al. | ................... | 600/7 |

OTHER PUBLICATIONS

Ilker Tunay, "Modeling magnetic catheters in external fields", in Conf Proc IEEE Eng Med Biol Soc. 2004;3:2006-9.*

* cited by examiner

*Primary Examiner* — Charles A Marmor, II
*Assistant Examiner* — Sunita Reddy
(74) *Attorney, Agent, or Firm* — Jeffrey Schox (57) ABSTRACT

A magnetic force control system for guiding a medical instrument within a body includes: a controlled magnet coupled to the medical instrument; a controller magnet that exerts a magnetic force on the controlled magnet; a magnetically permeable shield, placed between the controlled magnet and the controller magnet, that selectively modulates the magnetic force by rerouting magnetic field lines; and a control system. A method for guiding a medical instrument within a body with magnetic force control includes: providing a controlled magnet coupled to the medical instrument, inserting the controlled magnet and medical instrument into the body, providing a controller magnet outside the body, placing a magnetically permeable shield between the controlled magnet and the controller magnet, applying magnetic force, and selectively modulating the magnetic force with the shield to vary at least one of amplitude and orientation of the magnetic force, thereby guiding the controlled magnet within the body.

20 Claims, 8 Drawing Sheets

SYSTEM AND METHOD FOR GUIDING A MEDICAL INSTRUMENT WITH MAGNETIC FORCE CONTROL

CROSS-REFERENCE TO RELATED APPLICATIONS

This application claims the benefit of U.S. Provisional Application No. 61/107,264, filed Oct. 21, 2008, which is incorporated in its entirety by this reference.

TECHNICAL FIELD

This invention relates generally to the medical field, and more specifically to an improved system and method for controlling magnetic force in the magnetically-guided medical procedure field.

BACKGROUND

One of the limitations of current permanent magnet systems for current magnetically-guided minimally invasive surgical procedures is that they lack the ability to provide variable force. In many applications, however, variable force is crucial for optimal manipulation and control. As an example, a physician may need to vary the amount of force they exert on a magnetic tip catheter, depending on the anatomy and type of catheter procedure. As another example, a magnet-tipped endoscopic microscope benefits from variable magnetic force control. If the microscope is pressed too forcefully against tissue, the tissue is too deformed to provide quality images; however, if the microscope is not pressed forcefully enough against tissue, the microscope does not make sufficient contact with the tissue to obtain quality images. An ideal magnetic system for such procedures would provide an appropriate amount of contact force between the microscope and the tissue to provide optimal image quality.

Current permanent magnet systems for magnetically-guided minimally invasive systems require large magnets, which complicate attempts to modulate the magnetic force with reasonable bandwidth due to their large size and high inertia.

Thus, there is a need in the surgical field to create an improved system and method for guiding a magnetically-guided medical instrument. This invention provides such an improved system and method.

DESCRIPTION OF THE PREFERRED EMBODIMENTS

The following description of preferred embodiments of the invention is not intended to limit the invention to these preferred embodiments, but rather to enable any person skilled in the art to make and use this invention.

Figure 1:
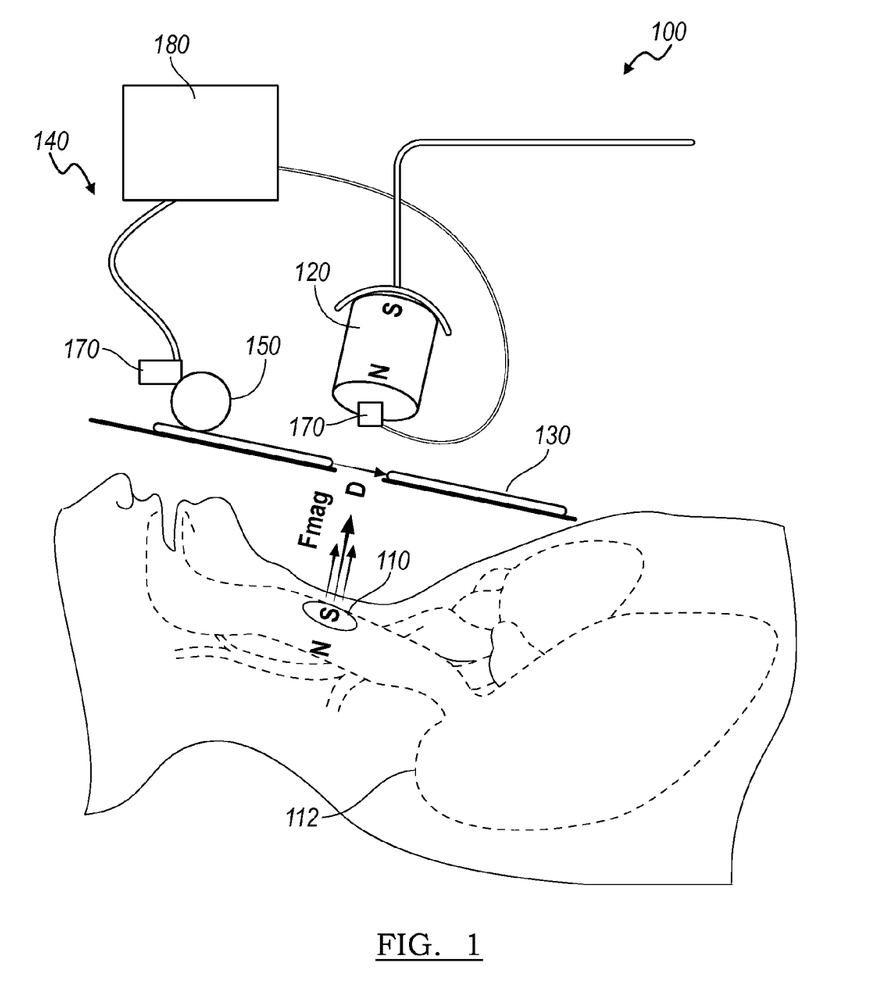
FIG. 1 is a schematic of the magnetic force control system of a preferred embodiment.

As shown in FIG. 1, the magnetic force control system 100 for guiding a medical instrument within a body for a medical procedure of the preferred embodiment preferably includes: a controlled magnet 110 coupled to the medical instrument and insertable into the body; a controller magnet 120 that exerts a controlling magnetic force on the controlled magnet 110; a magnetic shield 130, placed between the controlled magnet 110 and the controller magnet 120, that selectively modulates the magnetic force by rerouting magnetic field lines a control system 140 including an actuator 150 that varies the relative orientations of the shield 130 and the controller magnet 120, a sensor system 170 that measures at least one of the magnetic force and actuator position, and a controller 180 that controls the modulation of the magnetic force. The system 100 is preferably used for minimally-invasive procedures involving navigation through a body cavity, cardiovascular system, or any suitable passageway 112 in a patient. For example, the system may be used with cardiac ablation with a cardiac catheter or other catheter procedures, or endoscopic microscope or image capture procedures. However, the system may alternatively be used for any suitable procedure with any suitable medical instrument.

Figure 2:
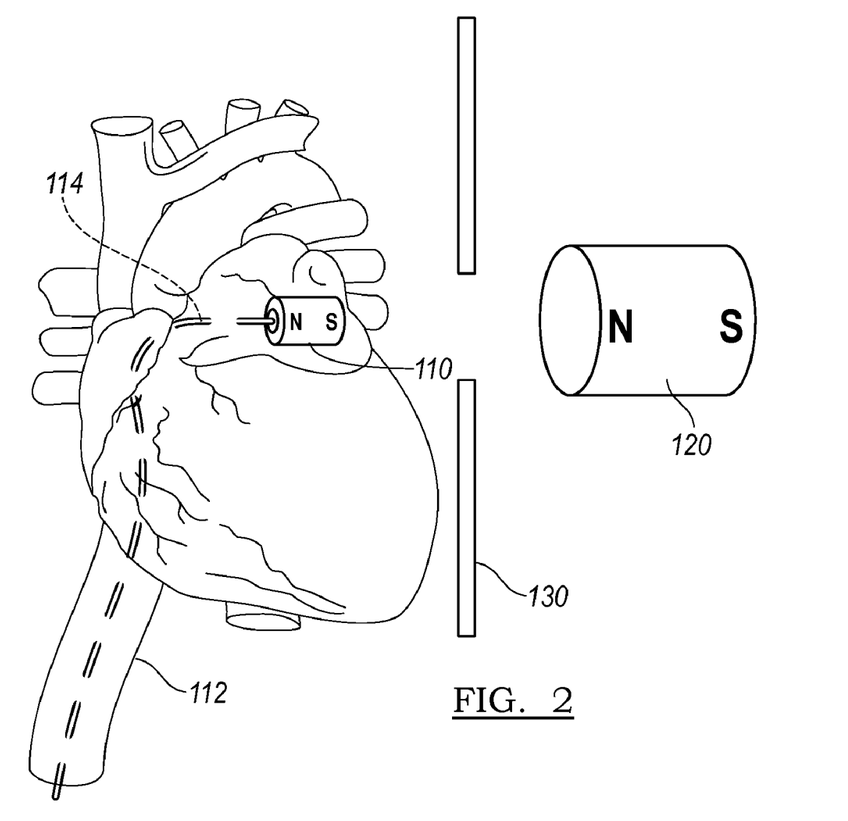
FIG. 2 is a partial side view of a cardiac catheter incorporating the magnetic force control system of a preferred embodiment.
Figure 3:
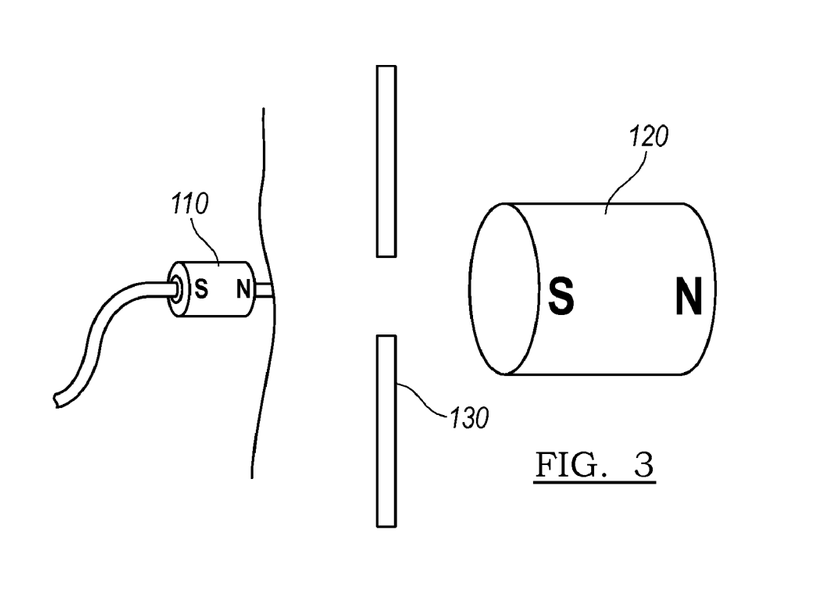
FIG. 3 is a partial side view of an endoscope incorporating the magnetic force control system of a preferred embodiment.
Figures 4A, 4B:
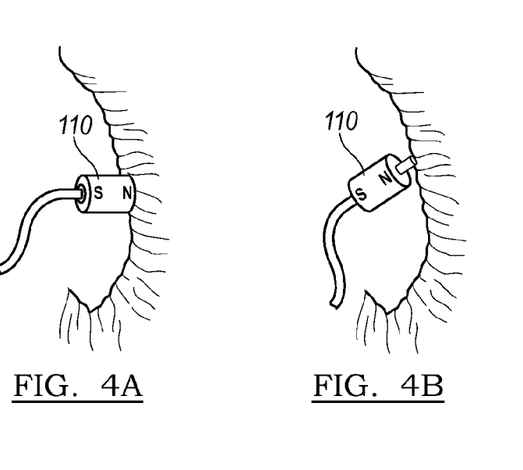
FIGS. 4A-4C are partial side views of situations of excess force, insufficient force, and optimal amount of force for an endoscope incorporating the magnetic force control system of a preferred embodiment.
Figure 4C:
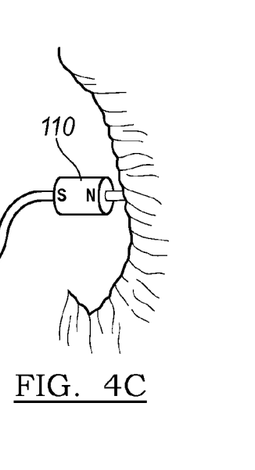
Figure 5:
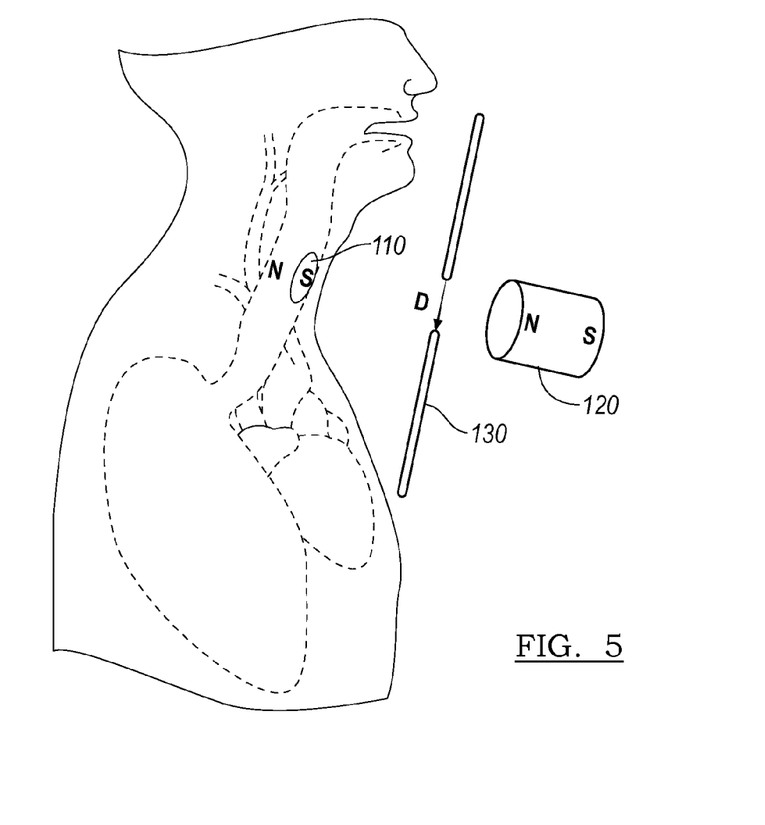
FIG. 5 is a partial side view of a "pill camera" incorporating the magnetic force control system of a preferred embodiment.

As shown in FIGS. 1-5, the controlled magnet 110 functions to couple to a medical instrument and move the medical instrument within the body. The controlled magnet 110 is preferably located on a navigating end 114 of the medical instrument, which is preferably the distal portion of the medical instrument, but may alternatively be any navigating portion of the medical instrument. For example, as shown in FIG. 2, the controlled magnet 110 is located on the distal end of a cardiac catheter. As a second example, as shown in FIG. 3, the controlled magnet 110 is located on the distal end of an endoscope to provide an ideal amount of contact force between the microscope and the tissue to provide optimal image quality. As shown in FIG. 4, finer force control for an endoscopic microscope is desirable to obtain quality images, because too much magnetic force deforms the observed tissue (FIG. 4A) and too little magnetic force does not let the microscope make sufficient contact with the tissue (FIG. 4B). An ideal amount of contact force between the microscope and the tissue provides optimal image quality (FIG. 4C). As a third example, as shown in FIG. 5, the controlled magnet 110 is on a small camera or "pill camera" that images the inside of a passageway 112 within the body of a patient, such as the gastrointestinal tract. The controlled magnet 110 may, however, be coupled to any suitable medical instrument. The system may include more than one controlled magnet, strategically placed on the medical instrument, which may increase control of the medical instrument. For example, multiple controlled magnets distributed along the length of a catheter may be simultaneously controlled to guide the catheter through the cardiovascular system.

The controlled magnet 110 is preferably a permanent magnet, and more preferably a neodymium permanent magnet with high magnetic field strength, on the order of grade N42. However, the controlled magnet 110 may alternatively be an electromagnet or any suitable magnetic material, or any suitable magnetic field strength. The controlled magnet 110 is preferably ferromagnetic or ferrimagnetic, but may alternatively be paramagnetic or diamagnetic. The controlled magnet 110 is preferably small enough to navigate a passageway 112 within the body of the patient, but particular size and shape of the controlled magnet 110 depends on the specific application of the system. As an example, the controlled magnet on the distal end of a catheter or endoscope may be cylindrical.

The controller magnet 120 functions to exert a controlling magnetic force on the controlled magnet 110. As shown in FIGS. 1 and 5, the controller magnet 120 is preferably located outside of the body, near enough to exert a magnetic force on the controlled magnet 110, and preferably has a higher magnetic field strength than the controlled magnet 110 such that the controller magnet 120 dominates the controlled magnet 110. In one variation, as shown in FIG. 1, the controller magnet 120 is secured to a stand or another suitable static external apparatus, such that the controller magnet 120 is secured in one stationary position. In a second variation, the controller magnet 120 is secured to a track 152 (FIGS. 6 and 7), disc 154 (FIG. 8), swing, moving arm, or another suitable movable external apparatus, such that the controller magnet 120 is movable relative to the body. The controller magnet 120 is preferably larger in size than the controlled magnet 110, but may alternatively be equal in size to or smaller than the controlled magnet 110. The controller magnet 120 is preferably the same type of magnet as the controlled magnet 110, but may alternatively be a different type. The controller magnet is preferably cylindrical, but may have any suitable specifications depending on the specific application of the system. The system may include more than one controller magnet, such as multiple controller magnets placed strategically at different locations and/or angles external to the body, to provide finer control and/or more coverage of control.

Figure 9:
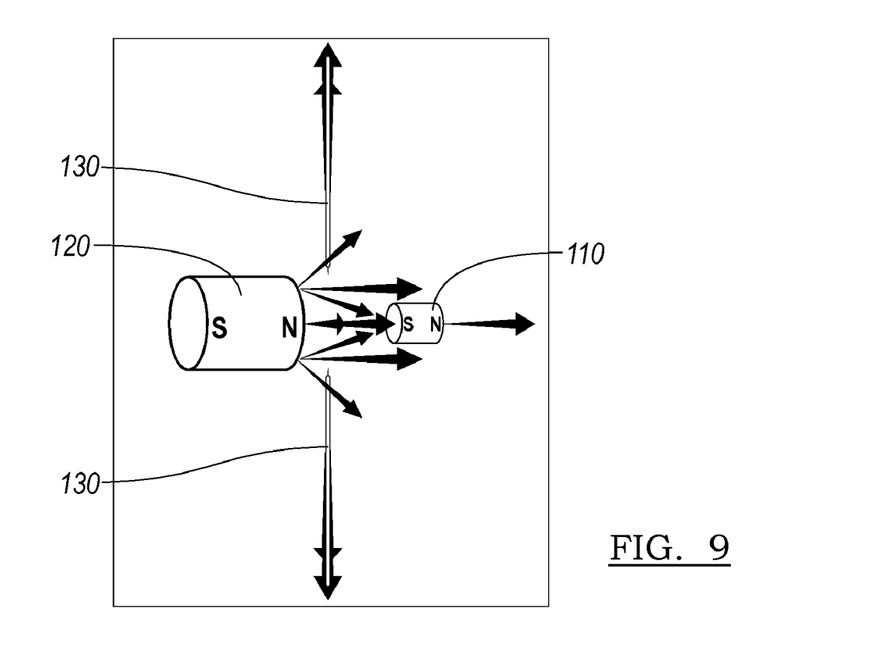
FIG. 9 is a representation of the magnetic shield rerouting magnetic field lines in the magnetic force control system.
Figure 10A:
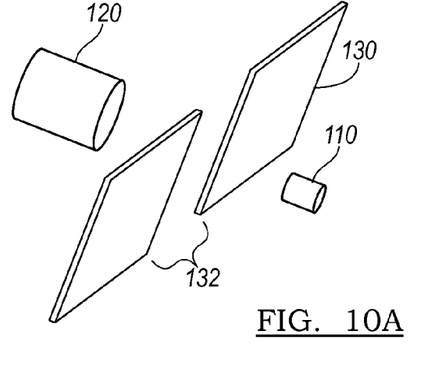
FIGS. 10A and 10B are examples of the translating variation of the magnetic shield in the magnetic force control system.
Figure 11A:
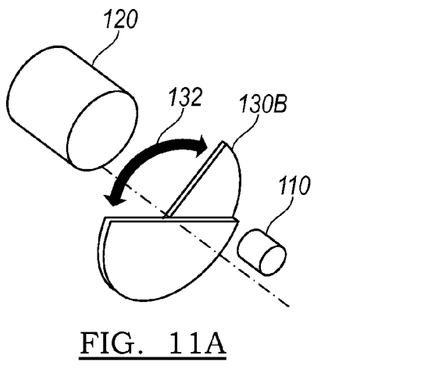
FIGS. 11A through 11C are examples of the rotating variation of the magnetic shield in the magnetic force control system.

The magnetic shield 130 functions to selectively modulate magnetic force between the controller magnet 120 and the controlled magnet 110 by rerouting magnetic field lines away from the controlled magnet, thereby reducing magnetic force on the controlled magnet. As shown in FIG. 9, the magnetic shield 130 preferably reroutes magnetic field lines away from the controlled magnet no by carrying at least a portion of the magnetic field lines within itself. The magnetic shield 130 preferably reroutes magnetic field lines due to having a higher magnetic permeability than the air or other substances between the controlled magnet and the controller magnet. The magnetic shield 130 is preferably placed substantially between the controlled magnet no and the controller magnet 120 to interfere with magnetic field lines, but may alternatively be placed in any suitable location relative to the controlled magnet and the controller magnet 120. By controlling the quantity and location of magnetic shielding between the controller magnet 120 and the controlled magnet no, the amount of force reduction between the magnets is controlled. The magnetic shield 130 preferably selectively modulates a varied amount of magnetic force between the controller magnet 120 and the controlled magnet no by being moved by the actuator 150 of the control system 140. The system preferably includes at least one magnetic shield for each controlled magnet, but may alternatively include any suitable number of magnetic shields. Multiple magnetic shields may operate individually and/or in tandem, such as multiple magnetic shields stacked in series between a controller magnet and a controlled magnet. The magnetic shield 130 is preferably mounted on a movable apparatus external to the body, such as a track, swing, bearing, or any suitable apparatus that facilitates movement of the magnetic shield 130. The magnetic shield 130 may be symmetrical, to avoid asymmetrical magnetic forces that could possibly pull the controlled magnet 110 in an unintended direction relative to the controller magnet 120. The magnetic shield 130 may be at least one of several variations. In some variations, as shown in FIGS. 10A and 11A, the magnetic shield 130 may define a gap that the actuator 150 opens and closes to modulate the magnetic force. In some variations, the magnetic shield 130 may have a generally uniform thickness, while in other variations the magnetic shield 130 may have a generally non-uniform thickness.

Figure 10B:
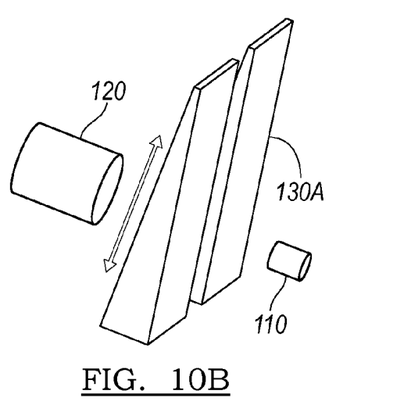

In a first variation, as shown in FIGS. 10A and 10B, at least a portion of the magnetic shield 130 moves in translation. The translation is preferably in a plane generally perpendicular to an axis that directly connects the controller magnet 120 and the controlled magnet 110. For example, as shown in FIG. 10A, the magnetic shield 130 may include two movable sheets that define a gap between the two sheets and translate to open and close the gap, thereby modulating the magnetic force. As another example, as shown in FIG. 10B, the magnetic shield 130A may include a movable wedge or other suitable piece having a nonuniform thickness that translates to vary the thickness of the shield 130 that passes between the controller magnet 120 and the controlled magnet 110, thereby modulating the magnetic force. In this variation, at least a portion of the magnetic shield 130 may additionally and/or alternatively move in translation along the axis that directly connects the controller magnet 120 and the controlled magnet 110, or any suitable translation direction.

Figure 11B:
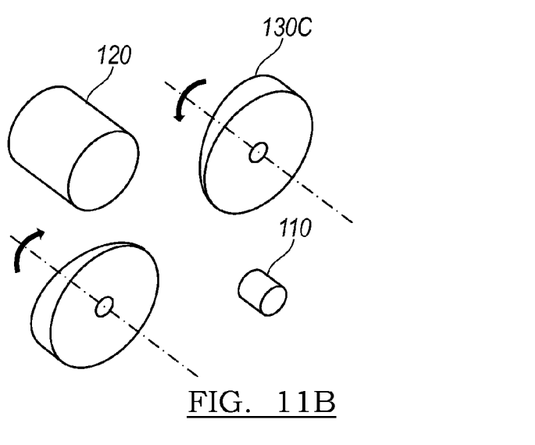
Figure 11C:
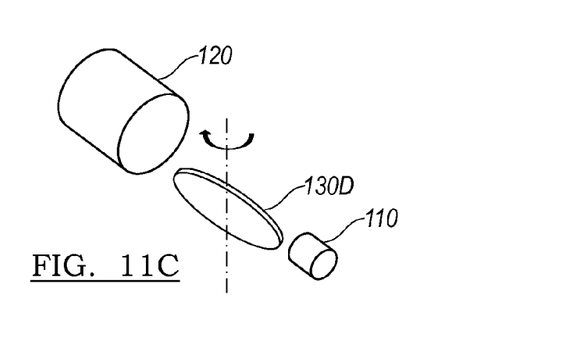

In a second variation, as shown in FIGS. 11 through 11C, at least a portion of the magnetic shield 130 moves in rotation. The rotation is preferably in a plane generally perpendicular to an axis that directly connects the controller magnet 120 and the controlled magnet 110. For example, as shown in FIG. 11A, the magnetic shield 130B may include an approximately circular disc that defines a gap in the shape of a circle segment, such that a portion of the disc rotates to open and close the gap, thereby modulating the magnetic force. As another example, as shown in FIG. 11B, the magnetic shield 130C may include two wedge-like discs or other suitable pieces of non-uniform thickness that rotate to vary the thickness of the shield 130 that passes between the controller magnet 120 and the controlled magnet 110, thereby modulating the magnetic force. As another example, as shown in FIG. 11C, the magnetic shield 130D may include a piece that is angled and/or has a variable thickness to form a "valve" that rotates about a second axis generally perpendicular to an axis that directly connects the controller magnet 120 and the controller magnet 120, or another suitable axis, such that rotation changes the projected area that passes between the controller magnet 120 and controlled magnet 110. In this example, the rotation of the angled magnetic shield 130D may be rapid and controlled in a particular fashion to produce a magnetic force drive similar to pulse-width modulation (PWM) as known to one ordinarily skilled in the art of motor drives. In this variation, at least a portion of an angled and/or variable thickness magnetic shield 130D may additionally and/or alternatively rotate in any suitable rotation direction.

Figure 12:
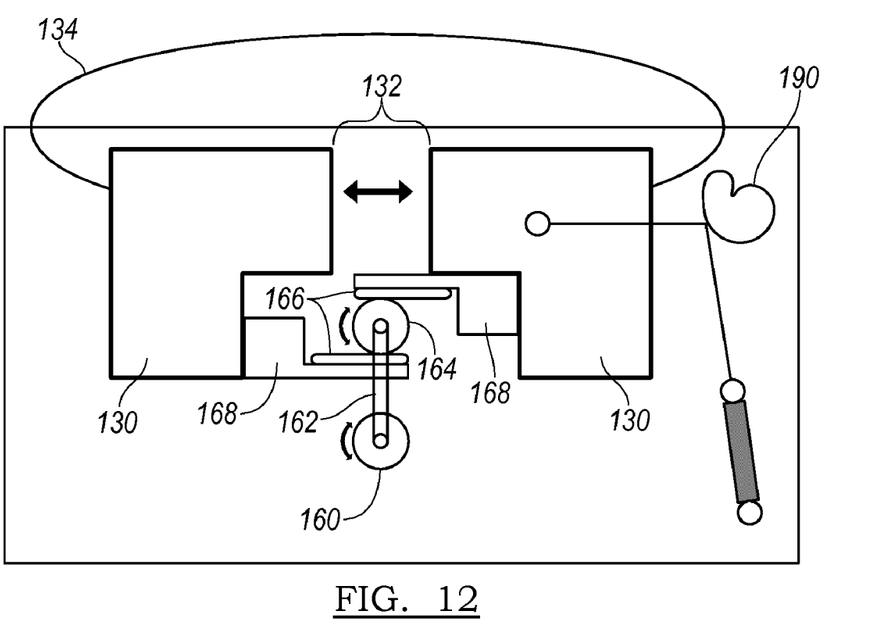
FIG. 12 is a detailed view of an actuator-controlled magnetic shield in the magnetic force control system.

The magnetic shield 130 may include a continuous path for rerouted magnetic field lines, which enables the rerouted magnetic field lines to form a complete circuit. The completion of a circuit helps improve system performance by enhancing the rerouting of magnetic field lines. As shown in FIG. 12, completion of a circuit may be accomplished by connecting a piece of material of high magnetic permeability and high magnetic saturation (such as a loop of wire of material such as Hymu-80, Hyperco-50, or Nickel-50) on two sides of the magnetic shield 130 where magnetic field lines are rerouted through the magnetic shield.

The magnetic shield 130 preferably includes a material that has high magnetic permeability and/or high magnetic saturation (on the order of a material such as Hymu-80, Hyperco-50, or Nickel-50), magnetic properties that increase the ability of the shield 130 to reroute magnetic field lines. However, the shield 130 may be made of any suitable material. As described in the above variations, the magnetic shield 130 may include one piece, multiple separate pieces, or multiple coupled pieces.

The control system 140 functions to oversee the modulation of the magnetic force. The control system 140 preferably includes an actuator 150, a sensor system 170, and a controller. The actuator 150 preferably varies the relative orientations of the shield 130 and the controller magnet 120, and/or the proximity between the shield 130 and the controller magnet 120. The actuator 150 is preferably an electromechanical actuator, such as a servomotor, stepper motor or a solenoid, and is located far enough away from the controller magnet 120 and the controlled magnet 110 to avoid unintended magnetic interaction and interference between the actuator and magnets. However, the actuator 150 may be any suitable kind of actuator. The actuator 150 may additionally and/or alternatively be separately magnetically shielded to avoid magnetic interaction and interference. The actuator 150 may further include transmission elements such as gears, belts, pulleys, cables, and/or any suitable transmission elements. As an example, as shown in FIG. 12, a motor shaft is coupled to a first gear 160, which drives a second pinion gear 164 with a belt 162. The second pinion gear 164 controls the width of gap 132 by engaging with linear rack gears 166 on spreaders 168 coupled to the magnetic shield 130. The actuator 150 is preferably a single actuator body, but may alternatively include multiple actuator bodies operating in tandem. In a first variation, as shown in FIG. 1, the actuator 150 is coupled to the magnetic shield 130 and is adapted to move at least a portion of the magnetic shield 130 relative to the controller magnet 120 in translation and/or rotation, as described above.

Figure 6:
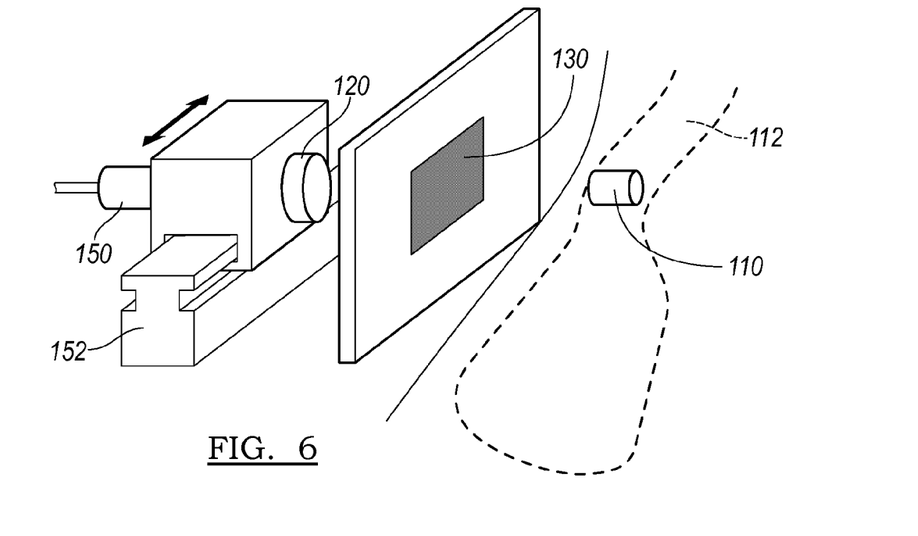
FIGS. 6-8 are schematics of examples of the second variation of the controller magnet in the magnetic force control system.
Figure 7:
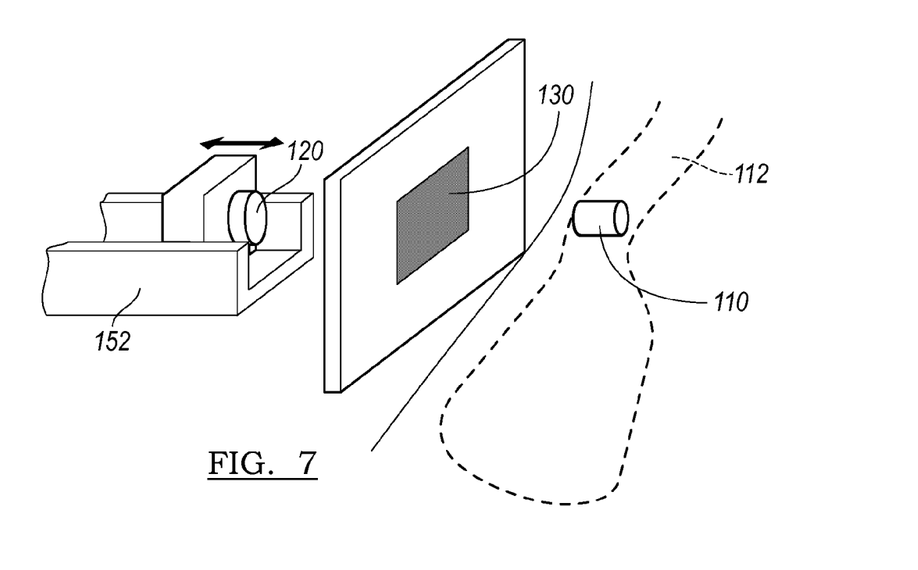
Figure 8:
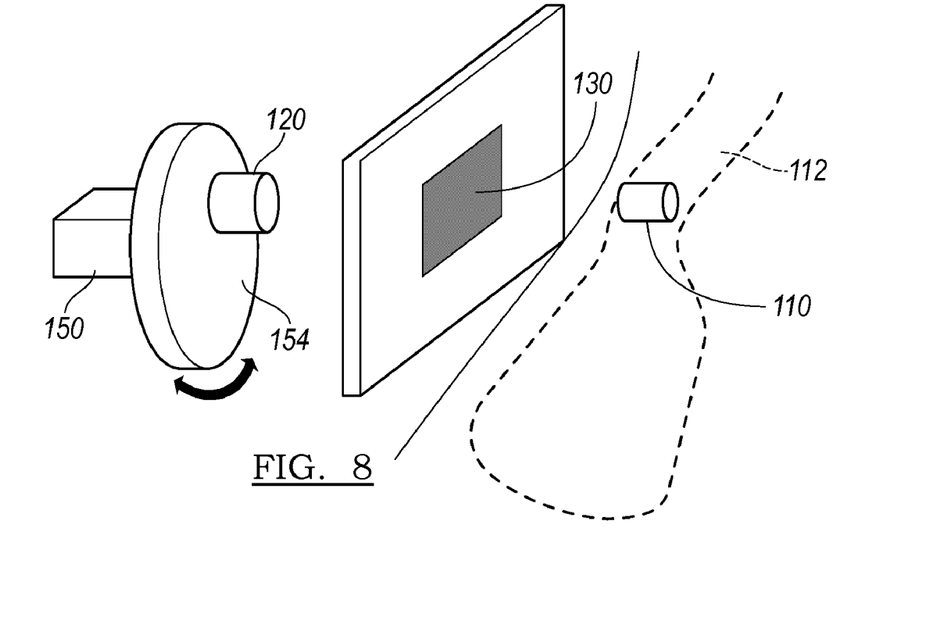

In a second variation, the actuator 150 is coupled to the controller magnet 120 and is adapted to move the controller magnet 120 relative to the magnetic shield 130. In this variation, the actuator 150 may move the controller magnet in one or more of the following directions: translation in a plane adjacent to the magnetic shield 130 (as shown in FIG. 6); translation along an axis such that the controller magnet 120 moves closer to or farther away from the magnetic shield 130 (as shown in FIG. 7); rotation in a plane adjacent to the magnetic shield 130 (as shown in FIG. 8); or any other suitable motion relative to the magnetic shield 130.

Figure 13:
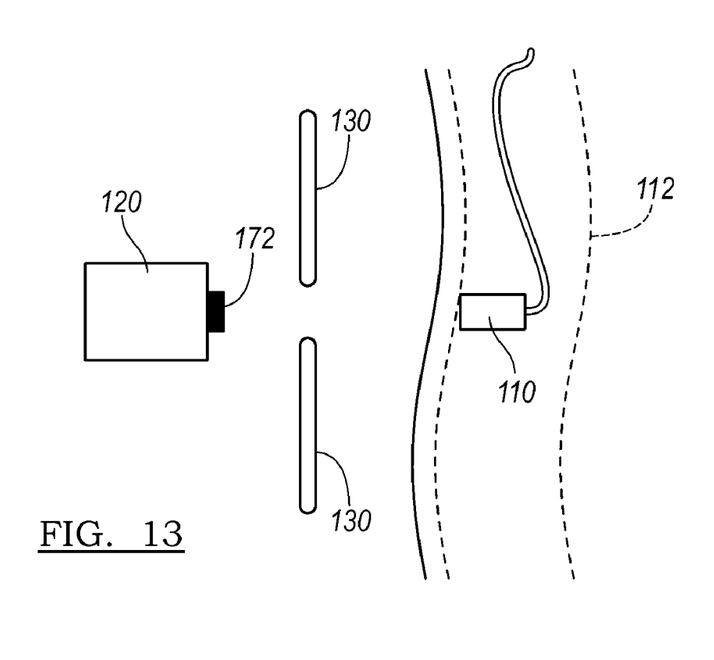
FIG. 13 is a side schematic partial view of the magnetic force control system.

The sensor system 170 of the control system 140 preferably functions to measure at least one of the magnetic force and actuator position, and more preferably measures both. The sensor system 170 preferably includes a magnetic force sensor and an encoder, but may additionally and/or alternatively include any suitable sensor. Measurement of the magnetic force preferably includes direction and/or magnitude of the magnetic force. The actuator position measured by the sensor system 170 may be indexed such as to provide calculated estimates of the actuator operation, such as actuator speed and/or acceleration. The measurements of the sensor system 170 are preferably used as feedback for the controller of the control system 140. In a first variation, as shown in FIG. 13, the sensor system 170 directly measures the magnetic force with the magnetic force sensor 172 placed on the controller magnet 120. In a second variation, the sensor system 170 determines the magnetic force by weighing the entire force control system except the controlled magnet 110, preferably using load cells, to measure the pull that the controller magnet 120 and controlled magnet 110 exert on each other. However, the sensor system 170 may alternatively use any suitable method or mechanism of measuring magnetic force. The sensor system 170 preferably measures the actuator position with an optical encoder, but may alternatively use any suitable method or mechanism of measuring actuator position.

Figure 14:
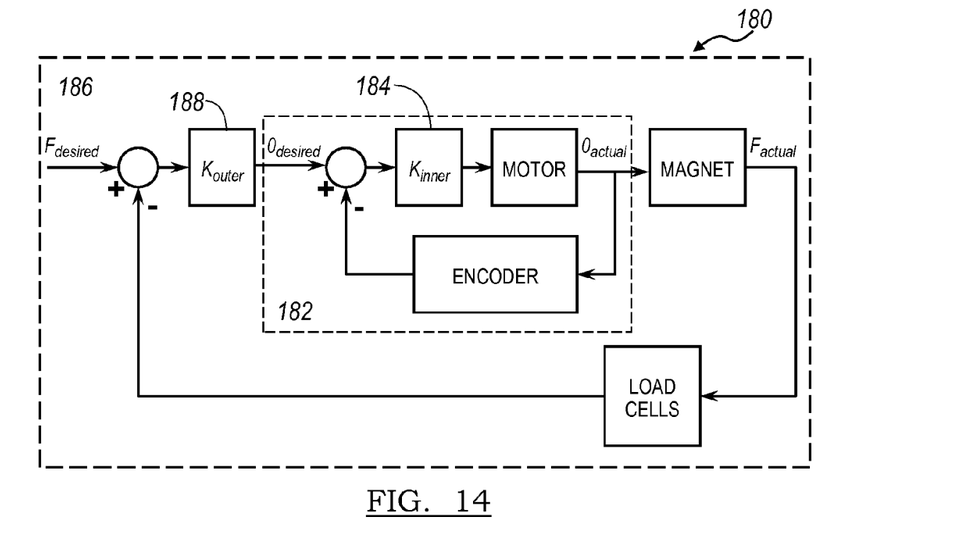
FIG. 14 is a schematic representation of the controller system architecture.

The controller 180 of the control system 140 functions to control the modulation of the magnetic force. The controller 180 preferably interprets the output of the sensor system 170 and communicates based on the output of the sensor system 170. The controller 180 preferably comprises a closed-loop control system architecture. As shown in FIG. 14, the controller 180 preferably incorporates a successive-loop closure architecture in which the inner loop 182 tracks actuator position, and the outer loop 186 tracks the magnetic force on the controlled magnet 110, but the controller may alternatively incorporate any closed-loop, open loop, or other suitable control algorithm. As one skilled in the art will know, the successive-loop closure architecture enables the inner loop and the outer loop to have different bandwidths. In the structure shown in FIG. 14, the inner loop requires faster dynamics to avoid system instability. The inner loop gain 184 is preferably a proportional-derivative (PD) controller, and the outer loop gain 188 is preferably a proportional-integral-derivative (PID) controller, but the gains for the inner and outer loops may alternatively be any suitable type of controller. Optimal inner loop and outer loop gain values may be empirically derived or experimentally derived.

As shown in FIG. 12, the control system 140 may further include a counterbalance device 190 to counteract magnetic shear forces exerted by the controller magnet 120 and controlled magnet 110 on the magnetic shield 130 in undesirable directions and magnitudes. The counterbalance device 190 is preferably a cable-driven dual capstan that converts the linear force profile of an extension spring into a force profile that will cancel out the shear forces on the magnetic shield 130, as in U.S. patent application Ser. No. 10/443,459, filed on 22 May 2003, now issued as U.S. Pat. No. 7,428,855, and entitled "Counter balance system and method with one or more mechanical arms", which is incorporated in its entirety by this reference. Alternative variations of the counterbalance system include springs directly attached to the magnetic shield 130, or any other suitable method of providing force to counteract magnetic shear forces on the magnetic shield.

Figure 15:
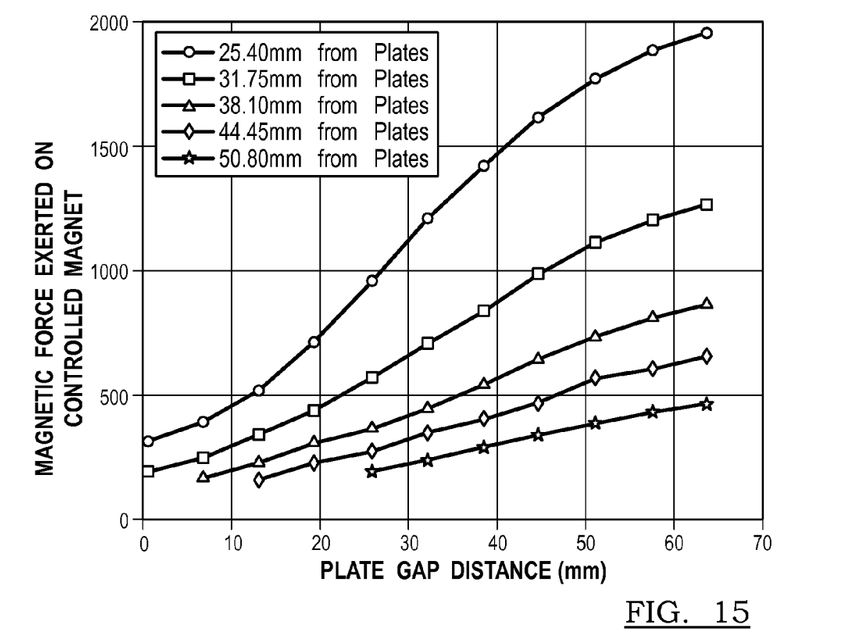
FIG. 15 is an example of a family of force-gap curves for an alternative application of the magnetic force control system.

Additional applications of the invention may take advantage of information obtained by using the magnetic force control system. For example, with the embodiment shown in FIG. 10A, one may position the controlled magnet 110 at a number of distances from the magnetic shield 130 and measure the corresponding magnetic force exerted on the controlling magnet (which is equal and opposite to that exerted on the controlled magnet) for various gap widths to obtain a family of force-gap curves, such as that shown in FIG. 15. Within this family of force-gap curves, each distinct curve corresponds to a distinct distance between the controller magnet 120 and controlled magnet 110. By measuring the force on the controlling magnet (thereby obtaining a measurement of the force exerted on the controlled magnet), and the gap distance for a particular configuration of the system and determining which force-gap curve contains the measured force and gap distance combination, one may estimate the distance between the controlled magnet 110 and controller magnet 120.

The method of guiding a medical instrument within a body with magnetic force control includes the steps of: providing a controlled magnet coupled to the medical instrument; inserting the controlled magnet and medical instrument into the body; providing a controller magnet outside the body; placing a magnetically permeable shield between the controlled magnet and the controller magnet; applying magnetic force to the controlled magnet with the controller magnet to influence the position of the controlled magnet; and selectively modulating the magnetic force with the shield to vary at least one of amplitude and orientation of the magnetic force, thereby guiding the controlled magnet within the body.

In one variation, the step of modulating the magnetic force includes the step of opening and closing a gap defined by the shield. The step of opening and closing a gap defined by the shield is preferably performed with an electromechanical actuator, controlled by a control system giving commands based on interpretations of a sensor system that measures magnetic force and/or actuator position.

In another variation, the step of modulating the magnetic force includes translating at least a portion of the shield. In another variation, the step of modulating the magnetic force includes rotating at least a portion of the shield. Similar to the step of opening and closing a gap defined by the shield, the steps of translating at least a portion of the shield and rotating at least a portion of the shield are preferably performed with an electromechanical actuator.

In another variation, the step of modulating the magnetic force includes moving the controller magnet relative to the magnetic shield. Similar to the step of opening and closing a gap defined by the shield, the step of moving the controller magnet relative to the magnetic shield is performed with an electromechanical actuator.

As a person skilled in the art will recognize from the previous detailed description and from the figures and claims, modifications and changes can be made to the preferred embodiments of the invention without departing from the scope of this invention defined in the following claims.

We claim:

1. A magnetic force control system for guiding a medical instrument within a body for a medical procedure, comprising:
    a controlled magnet, coupled to the medical instrument, that is insertable into the body;
    a controller magnet that exerts a magnetic force on the controlled magnet;
    a magnetically permeable shield, placed between the controlled magnet and the controller magnet, that selectively modulates the magnetic force by rerouting magnetic field lines; and
    a control system, having an actuator that varies the relative orientations of the shield and the controller magnet, a sensor system that measures at least one of the magnetic force and actuator position, and a controller that controls the modulation of the magnetic force.

2. The system of claim 1, wherein the medical instrument has a navigating end, wherein the controlled magnet is located on the navigating end.

3. The system of claim 1, wherein at least one of the controlled magnet and the controller magnet is a permanent magnet.

4. The system of claim 1, wherein the actuator is coupled to the shield and moves at least a portion of the shield in translation.

5. The system of claim 4, wherein the translation is in a plane generally perpendicular to an axis directly connecting the controller magnet and the controlled magnet.

6. The system of claim 4, wherein the translation is along an axis directly connecting the controller magnet and the controlled magnet.

7. The system of claim 1, wherein the actuator is coupled to the shield and moves at least a portion of the shield in rotation.

8. The system of claim 7, wherein the rotation is in a plane generally perpendicular to an axis directly connecting the controller magnet and the controlled magnet.

9. The system of claim 7, wherein the rotation is about a second axis generally perpendicular to a first axis directly connecting the controller magnet and the controlled magnet.

10. The system of claim 1, wherein the shield defines a gap that modulates the magnetic force; wherein the actuator is coupled to the shield such that the actuator selectively opens and closes the gap.

11. The system of claim 1, wherein the shield defines a continuous path for rerouted magnetic field lines that enables the rerouted magnetic field lines to form a complete circuit.

12. The system of claim 1, wherein the shield is of generally non-uniform thickness.

13. The system of claim 1, wherein the actuator is coupled to the controller magnet and moves the controller magnet relative to the shield.

14. The system of claim 1, wherein the sensor system includes a sensor on the controller magnet.

15. The system of claim 1, wherein the controller includes a successive-loop closure control algorithm.

16. A method for guiding a medical instrument within a body with magnetic force control, comprising the steps of:
    providing a controlled magnet coupled to the medical instrument;
    inserting the controlled magnet and the medical instrument into the body;
    providing a controller magnet outside the body;
    placing a magnetically permeable shield between the controlled magnet and the controller magnet;
    applying a magnetic force to the controlled magnet with the controller magnet to influence the position of the controlled magnet; and
    selectively modulating the magnetic force with the shield to vary at least one of amplitude and orientation of the magnetic force, thereby guiding the controlled magnet within the body.

17. The method of claim 16, wherein the step of modulating the magnetic force includes opening and closing a gap defined by the shield.

18. The method of claim 16, wherein the step of modulating the magnetic force further includes translating at least a portion of the shield.

19. The method of claim 16, wherein the step of modulating the magnetic force further includes rotating at least a portion of the shield.

20. The method of claim 16, wherein the step of modulating the magnetic force further includes moving the controller magnet relative to the shield.

* * * * *